United States Patent [19]

Noda et al.

[11] 4,165,428

[45] Aug. 21, 1979

[54] INDOLEACETIC ACID ESTER DERIVATIVES

[75] Inventors: Kanji Noda, Chikushino; Akira Nakagawa; Satoru Miyata, both of Tosu; Yoichi Nakashima, Tachiarai; Hiroyuki Ide, Fukuoka, all of Japan

[73] Assignee: Hisamitsu Pharmaceutical Co., Inc., Saga, Japan

[21] Appl. No.: 804,280

[22] Filed: Jun. 7, 1977

[30] Foreign Application Priority Data

Jun. 22, 1976 [JP] Japan .................................. 51-74104

[51] Int. Cl.² .................... C07D 209/28; C07D 213/79
[52] U.S. Cl. ........................... 546/273; 260/326.13 A; 424/263; 424/274
[58] Field of Search ........ 260/295 R, 295 B, 295.5 R, 260/326.13 A, 295.5 B; 546/273

[56] References Cited

U.S. PATENT DOCUMENTS

| 3,271,394 | 9/1966 | Shen | 260/326.13 A |
| 3,470,203 | 9/1969 | Gal et al. | 260/326.13 A |
| 3,910,952 | 10/1975 | Boltze et al. | 260/326.13 A |

OTHER PUBLICATIONS

The Merck Index, 8th Edition, p. 566, "Indomethacin".

Primary Examiner—Richard Raymond
Attorney, Agent, or Firm—Browdy and Neimark

[57] ABSTRACT

The present invention relates to the indoleacetic acid ester derivatives of the following general formula:

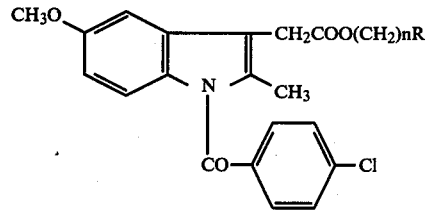

wherein n represents an integer from one to 3; R is selected from the group consisting of hydroxyl, halogen, trihalomethyl, alkoxy, acyloxy, substituted phenyl, pyridyl and substituted pyridyl. These compounds possess a high degree of pharmacological activities such as analgetic, anti-inflammatory and anti-pyretic activities as well as low side effects on the gastrointestinal tracts when given orally and topically, and therefore they may be useful as analgesics, anti-inflammatories and anti-pyretics for internal and external use.

1 Claim, No Drawings

INDOLEACETIC ACID ESTER DERIVATIVES

DETAILED DESCRIPTION

The present invention relates to novel indoleacetic acid ester derivatives represented by the general formula [A]:

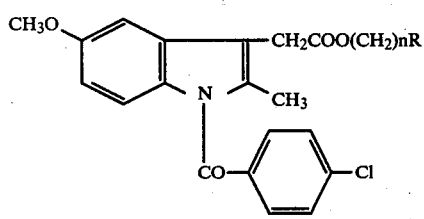

[A]

wherein n represents an integer from one to 3; R is selected from the group consisting of hydroxyl, halogen, trihalomethyl, alkoxy, acyloxy, substituted phenyl, pyridyl and substituted pyridyl.

More particularly, R in the aforesaid general formula [A] may be explained as follows. Halogen in R may be chlorine, fluorine, bromine or iodine. Trihalomethyl may be trichloromethyl or trifluoromethyl. Alkoxy may be lower alkoxy such as methoxy, ethoxy and propoxy. Acyloxy may be lower acyloxy such as acetoxy and propionyloxy. Substituted phenyl may be the phenyl substituted with one or two substituents at any positions. These substituents include halogen such as chlorine, fluorine, bromine and iodine, lower alkyl such as methyl and ethyl, lower alkoxy such as methoxy and ethoxy, and nitro and trifluoromethyl. Pyridyl may be 2-pyridyl, 3-pyridyl or 4-pyridyl. Substituted pyridyl may be the pyridyl such as 2-pyridyl, 3-pyridyl or 4-pyridyl substituted at any positions with one or two substituents. These substituents include halogen such as chlorine, fluorine, bromine and iodine, and methyl.

Predominant anti-inflammatory agents for external use have been adrenocortical hormones. However, long-term use of these steroid preparations often cause severe side effects. For this reason, development of anti-inflammatory agents for topical use which may be of less toxicity has been demanded in this medical field. Thus, the present inventors, paying our attention on the development of non-steroidal anti-inflammatory agents for topical use, have synthesized various novel compounds. As a result, we have found the aforesaid indoleacetic acid ester derivatives which possess a high degree of analgetic and anti-inflammatory activities when given both via oral and topical routes, and completed the present invention. All the compounds of the present invention are novel ones, which have not been found in any publications, and in addition the said compounds possess a high degree of analgetic and anti-inflammatory activities and cause little or no side effects on the gastrointestinal tracts when given orally. Therefore, the said compounds may be useful as medicines both for oral and topical use.

The processes for preparing the compounds of the present invention are explained in the following. The compounds of the present invention may be obtained in high yields by any one of the following processes.

Process [I]:

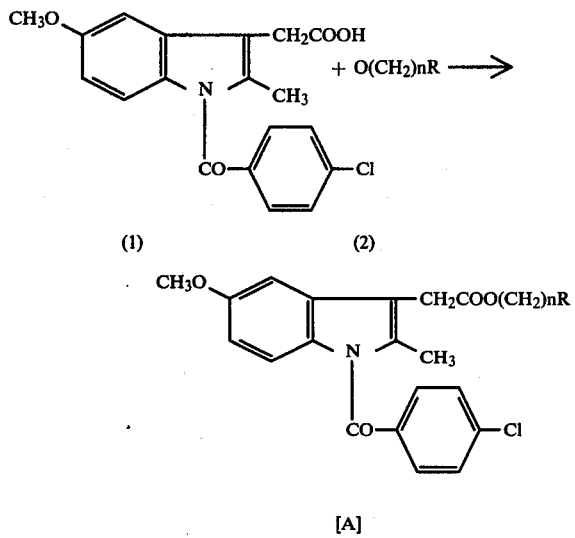

wherein n and R have the same meanings as defined above.

Process [II]:

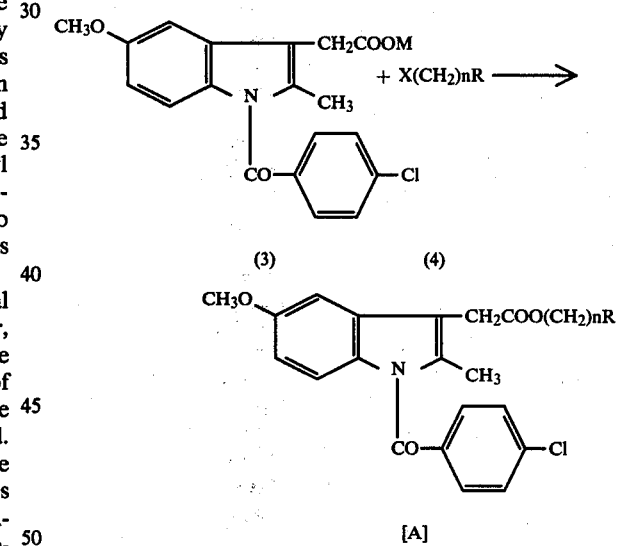

wherein n and R have the same meanings as defined above; M may be alkali metal; X may be halogen or organic sulfonyloxy.

Process [III]:

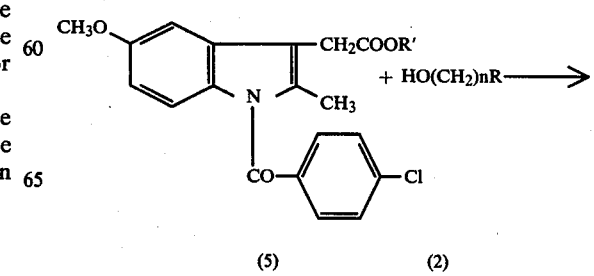

-continued

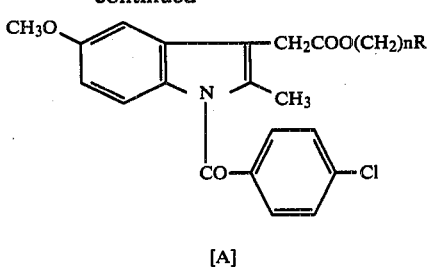

[A]

wherein n and R have the same meanings as defined above; R' may be lower alkyl.

Process [IV]:

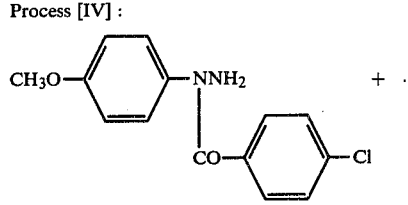

(6)

(7)

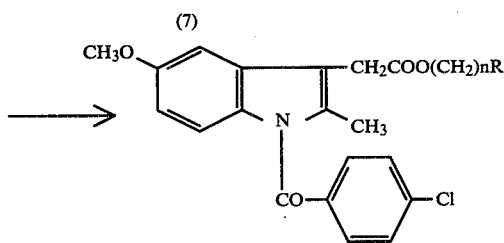

[A]

wherein n and R have the same meanings as defined above.

Further details of the processes shown by the aforesaid reaction schemes are given in the following.

In the aforesaid process (I), 1-(p-chlorobenzoyl)-2-methyl-5-methoxy-3-indolylacetic acid (1) or its reactive derivative (for example, acid halide and acid anhydride etc.) is allowed to react with the alcohols (2). When the acid anhydride of the compounds (1) is used as a reactant, it may be heated directly with the alcohols (2). When the acid halide of the compound (1) is used as a reactant, the reactions are preferably performed by using tertiary amines such as pyridine, trimethylamine and triethylamine as deacidifying agents.

A large excess of the alcohol (2) may serve as a reaction solvent. Other reaction solvents include tetrahydrofuran, diglyme, acetone, chloroform, benzene, toluene and xylene, which may not participate in the reaction itself.

In the aforesaid process (II), the compounds (1) are allowed to react with such metal compounds as sodium hydride and potassium hydride in the presence of such organic solvents as tetrahydrofuran, diglyme, benzene and toluene to give the compounds (3), which are further allowed to react with 1 to 3 moles of the comound (4) either by heating or under reflux.

In the aforesaid process (III), interesterification proceeds smoothly when the alcohols (2) are added in excess to the compound (5) and the mixture is heated.

In the aforesaid process [IV], N'-(p-chlorobenzoyl)-p-methoxyphenylhydrazine (6) or its salt (e.g. chloride, phosphate and the like) or its hydrazone derivative (e.g. hydrazone such as acetaldehyde or benzaldehyde) is allowed to react with a levulinic acid ester derivative of the general formula (7) in the absence or presence of condensing agents such as mineral acids (e.g., hydrochloric acid and sulfuric acid), metal halides (e.g. zinc chloride and copper chloride), borofluorides and polyphosphoric acids, in suitable solvents by application of heat at temperatures of 60° to 140° C. Preferable solvents include organic acids such as acetic acid and propionic acid, and organic solvents such as benzene, toluene, xylene, dioxane, isopropylether, acetonitrile, propanol, butanol and ethylene glycol ether. The reaction proceeds even in the absence of solvents.

COMPOUND

The compounds of the present invention may be prepared by any one of the processes [I]–[IV] described above, and the examples of the said compounds as well as melting point thereof are shown in Table I.

Table I

Examples of the compounds of the general formula [A] obtained by the present invention.

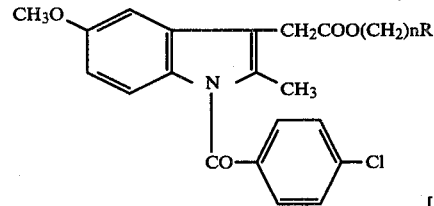

[A]

| Compound No. | n | R | Melting points (°C.) |
|---|---|---|---|
| 1 | 2 | —OH | 106–107 |
| 2 | 1 | —CF$_3$ | 97–98 |
| 3 | 1 | —OCH$_3$ | 98–99 |
| 4 | 2 | —OCH$_3$ | 68–69 |
| 5 | 1 | —OC$_2$H$_5$ | 62–63 |
| 6 | 2 | —OC$_2$H$_5$ | 77–78 |
| 7 | 2 | —OCOCH$_3$ | 119–121 |
| 8 | 1 | —C$_6$H$_4$Cl | 113–114 |
| 9 | 1 | —C$_6$H$_4$F | 102–103 |
| 10 | 1 | —C$_6$H$_4$F | 97–98 |
| 11 | 1 | —C$_6$H$_4$F | 122–123 |
| 12 | 2 | —C$_6$H$_4$F | 117–118 |

Table I-continued

Examples of the compounds of the general formula [A] obtained by the present invention.

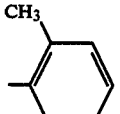

[A]

| Compound No. | n | R | Melting points (°C.) |
|---|---|---|---|
| 13 | 1 | 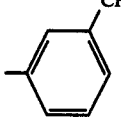 2-CH3-phenyl | 143-144 |
| 14 | 1 | 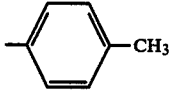 3-CH3-phenyl | 92-93 |
| 15 | 1 | 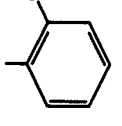 4-CH3-phenyl | 120-121 |
| 16 | 1 | 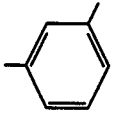 2-CF3-phenyl | 66-67 |
| 17 | 1 |  3-CF3-phenyl | 88-89 |
| 18 | 1 | 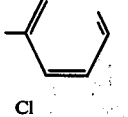 pyridyl | 95-96 |
| 19 | 1 | 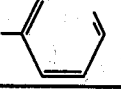 pyridyl | 116-118 |
| 20 | 1 | Cl-pyridyl | 119-121 |

All of the compounds of the present invention were first tested for their acute toxicities, and subsequently for their anti-inflammatory activities. In addition, ulcerogenic activities inherent in conventional non-steroidal anti-inflammatories were examined. It is found that certain of the compounds of the present invention have shown a high degree of pharmacological activities with low toxicity. The testing methods are described in the following, and the results are summarized in Table II.

(1) ACUTE TOXICITY

Each test compound suspended in 1% tragacanth-saline was administered intraperitoneally or orally to male mice of ddY-strain (body weight 16–24 g). The lethal dose was estimated from the death of animals 72 hours following administration.

(2) ANTI-INFLAMMATORY ACTIVITY FOR ORAL ROUTE

A group of five male rats of Wistar-strain (body weight 100–150 g) were orally given each test compound suspended in 0.5% tragacanth-saline. After one hour 1.0% carrageenin suspended in the water for injection was injected subcutaneously to a hind paw. After 3 hours the carrageenin edema was measured by volume, and the percent inhibition was determined with respect to the results for the control animals. For comparison, the percent inhibition of each test compound of the present invention was divided by that of the reference compound, indomethacin, to give the relative inhibition, which is included in Table II. The mean percent inhibition of indomethacin was 41.1% at 10 mg/kg.

(3) ULCEROGENIC ACTIVITY ON RAT STOMACH

Male Wistar rats weighing 200–220 g were fasted for 24 hours. Indomethacin and the test drugs were suspended with 0.5% tragacanth solution, and these suspensions were given the animals orally at each dose of 20 mg/kg. The animals were sacrificed with ether 18 hours after administration. The excised stomachs were filled with 1% formalin solution and the whole were immersed in the 1% formalin solution for fixation. Thereafter, an incision was made parallel to the greater curvature to examine whether or not an erosion or ulcer occurs. The degree of erosion and ulcer was represented by the sum of area ($mm^2$).

Table II

Pharmacological Effects and Acute Toxicity of the Object Compound, Indoleacetic Acid Ester Derivatives obtained by the Present Invention:

| Standard compound | anti-inflammatory effect for oral route (10mg/kg) | gastric ulcer index (mm$^2$) | acute toxicity for oral route (mg/kg) |
|---|---|---|---|
| indomethacin | 1.0 | 6.75 ± 1.98 | 10–20 |

Object Compound of General Formula [A]:

CH$_3$O—[indole with CH$_2$COO(CH$_2$)$_n$R at 3-position, CH$_3$ at 2-position, N-CO-C$_6$H$_4$-Cl (p)]

| n | R | [A] (10mg/kg) | (mm$^2$) | (mg/kg) |
|---|---|---|---|---|
| 1 | 2-F-phenyl | 0.76 | 0.50 ± 0.30 | >500 |
| 1 | 3-F-phenyl | 0.68 | 0.50 ± 0.38 | >500 |
| 1 | 4-F-phenyl | 0.41 | 0.13 ± 0.08 | >500 |
| 1 | 2-CH$_3$-phenyl | — | 0.19 ± 0.13 | >500 |
| 1 | 3-CH$_3$-phenyl | — | 0.13 ± 0.08 | 200–500 |
| 1 | 4-CH$_3$-phenyl | 1.00 | 0.88 ± 0.39 | 500 |

Examples of the compounds of the present invention are illustrated in the following.

EXAMPLE 1

A mixture of 3.0 g of 1-(p-chlorobenzoyl)-2-methyl-5-methoxy-3-indolylacetic acid and 3.0 g of thionyl chloride was refluxed in 70 ml of benzene for 3 hours. After cooling, the solvent was distilled off under reduced pressure to leave a residue. The residue was dissolved in 20 ml of tetrahydrofuran. This solution was added to a solution of 1.0 g of 3-pyridylmethanol in 70 ml of tetrahydrofuran under cooling. To this mixture was carefully added 0.95 g of triethylamine and stirring was continued for 2 hours at room temperature. After the reaction was complete, the solvent was removed by distillation under reduced pressure to leave a residue. After addition of water to the residue, an oily substance was obtained and extracted with chloroform. The extract was applied on a column of silica gel and the adsorbate was eluted with ether to give crystals. Recrystallization of the crystals from a mixed solvent of ethyl acetate ester and ether yielded 3.0 g of 1-(p-chlorobenzoyl)-2-methyl-5-methoxy-3-indolylacetic acid-3-pyridylmethyl ester, melting at 116°–118° C. Analysis—Calculated for C$_{25}$H$_{21}$ClN$_2$O$_4$: C, 66.89; H, 4.72; N, 6.24. Found: C, 67.06; H, 4.68; N, 6.11.

EXAMPLE 2

To a mixture of 3.6 g of 1-(p-chlorobenzoyl)-2-methyl-5-methoxy-3-indolylacetic acid and 50 ml of dry tetrahydrofuran was added 0.5 g of 50% sodium hydride and the mixture was stirred for 30 minutes. To this mixture was further added 2.5 g of chloromethylethyl ether and the whole was reacted for 3 hours at room temperature. After the reaction was complete, the solvent was removed by distillation under reduced pressure. The residue thus obtained was neutralized with diluted hydrochloric acid, and then extracted with ethyl ether. The ether layer separated was washed with water and dried. The ether was removed by distillation to yield crystals. Recrystallization of the crystals from petroleum ether yielded 3.0 g of 1-(p-chlorobenzoyl)-2-methyl-5-methoxy-3-indolylacetic acid-ethoxymethyl ester as colorless prisms, melting at 60°–61° C. Analysis—Calculated for $C_{22}H_{22}ClNO_5$: C, 63.48; H, 5.17; N, 3.42. Found: C, 63.53; H, 5.33; N, 3.37.

EXAMPLE 3

A mixture of 1.0 g of N'-(p-chlorobenzoyl)-p-methoxyphenylhydrazine chloride, 0.85 g of levulinic acid-p-methylbenzyl ester and 6 ml of glacial acetic acid was reacted at 80° C. for 3 hours. After the reaction was complete, the solvent was removed by distillation under reduced pressure from the mixture to leave a residue. To the residue was added ice-water, and the residue was extracted with ether. The ether extract was washed with 5% sodium bicarbonate and with water, and subsequently dehydrated. The ether was distilled off from the extract to leave a residue. The residue was then applied on a column of silica gel, and the adsorbate was eluted with ether. The first effluent was concentrated, and on cooling to room temperature 1.32 g of 1-(p-chlorobenzoyl)-2-methyl-5-methoxy-3-indolylacetic acid-p-methylbenzyl ester as colorless needles, melting at 119°–120° C. Mass spectrum: parent ion 461 m/e.

EXAMPLE 4

A mixture of 1.0 g of N'-(p-chlorobenzoyl)-p-methoxyphenylhydrazine chloride, 0.93 g of levulinic acid-p-chlorobenzyl ester and 6 ml of glacial acetic acid is reacted at 80° C. for 3 hours. After the reaction was complete, the solvent was removed by distillation under reduced pressure to leave a residue. To the residue was added ice-water and the whole was extracted with ether. The ether extract was washed with 5% sodium bicarbonate solution and water and then dehydrated. The ether was removed by evaporation to leave a residue. The residue was recrystallized from a mixed solvent of ether and isopropyl ether to yield 1.35 g of 1-(p-chlorobenzoyl)-2-methyl-5-methoxy-3-indolylacetic acid-p-chlorobenzyl ester as colorless needles, melting at 113°–114° C. Mass spectrum: parent ion 481 m/e.

What is claimed is:
1. A compound of the following formula:

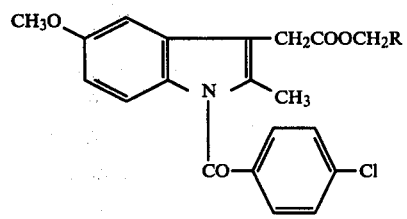

wherein R is pyridyl or phenyl substituted with one or two substituents at any position, said substituents being selected from the group consisting of fluorine, methyl and trifluoromethyl.

* * * * *